United States Patent [19]

Nicholson et al.

[11] Patent Number: 5,268,001
[45] Date of Patent: Dec. 7, 1993

[54] BONE FASTENER

[75] Inventors: James E. Nicholson, Lincoln; Rickey D. Hart, North Attleboro, both of Mass.

[73] Assignee: Innovasive Devices, Inc., Hopkinton, Mass.

[21] Appl. No.: 765,445

[22] Filed: Sep. 25, 1991

Related U.S. Application Data

[63] Continuation-in-part of Ser. No. 588,025, Sep. 25, 1990, abandoned.

[51] Int. Cl.⁵ .................. A61B 17/56; A61F 2/32
[52] U.S. Cl. .................................. 606/72; 606/104
[58] Field of Search ............... 606/62, 63, 72, 73, 606/65, 70, 71, 69, 77, 104, 75, 76; 623/16-23

[56] References Cited

U.S. PATENT DOCUMENTS

| | | |
|---|---|---|
| 3,036,482 | 5/1962 | Kenworthy et al. |
| 4,140,111 | 2/1979 | Morrill |
| 4,590,928 | 5/1986 | Hunt et al. |
| 4,632,100 | 12/1986 | Somers et al. |
| 4,662,886 | 5/1987 | Moorse et al. |
| 4,716,893 | 1/1988 | Fischer et al. |
| 4,738,255 | 4/1988 | Goble et al. |
| 4,741,330 | 5/1988 | Hayhurst |
| 4,778,468 | 10/1988 | Hunt et al. |
| 4,834,752 | 5/1989 | Van Kampen |
| 4,858,603 | 8/1989 | Clemow et al. |
| 4,898,156 | 2/1990 | Gatturna et al. |
| 4,899,743 | 2/1990 | Nicholson et al. |
| 4,924,865 | 5/1990 | Bays et al. |
| 4,940,467 | 7/1990 | Tronzo |
| 4,944,742 | 7/1990 | Clemow et al. |
| 5,013,316 | 5/1991 | Goble et al. |

FOREIGN PATENT DOCUMENTS

WO89/01767 3/1989 World Int. Prop. O.

OTHER PUBLICATIONS

Daniel, et al. "Fixation of Soft Tissue", 1987, The Anterior Cruciate Deficient Knee, New Concepts in Ligament Repair, Ch. 8, pp. 114-125.

Bankhart, "Recurrent Dislocation of Shoulder: The Pathology and Treatment of Recurrent Dislocation of the Shoulder-Joint" 1938, British J. Surgery, vol. 26, pp. 23-29.

Rowe, et al., "Recurrent Anterior Dislocation of the Shoulder After Surgical Repair", Feb. 1984, J. Bone and Joint Surgery, vol. 66-A, No. 2, pp. 159-168.

Venable, et al., "The Effects on Bone of the Presence of Metals; Based upon Electrolysis", Jan.-Jun. 1937, Annals of Surgery, vol. 105, 917-938.

Primary Examiner—Michael A. Brown
Attorney, Agent, or Firm—Choate, Hall & Stewart

[57] ABSTRACT

A bone fastener for fixing either a suture or a rivet within a predrilled bone hole includes an expandable sleeve having an axial bore and a pin forcibly insertible into the axial bore, the expandable sleeve being configured to be insertible into a bore drilled in bone, at least a portion of the pin having an outer diameter greater than the inner diameter of at least a portion of the axial bore. The fastener is emplaced by inserting the sleeve into a predrilled hole in the bone, and then forcing the pin into the axial bore, so that the wider portion of the pin presses outward against and expands the narrower portion of the sleeve, causing the sleeve to forcibly contact the walls of the bone hole and fixing the pin and sleeve firmly in place within the hole. Also, apparatus for emplacement of such a fastener includes a holder for holding the expandable sleeve in position within the predrilled hole in the bone, and a plunger moveable in relation to the holder for forcing the pin into the bore, so that the pin can be forced into the axial bore without imposing substantial net forces toward or away from the bone.

9 Claims, 9 Drawing Sheets

BONE FASTENER

This application is a continuation-in-part of our copending U.S. patent application Ser. No. 588,025, filed Sep. 25, 1990, now abandoned.

BACKGROUND OF THE INVENTION

This invention relates to fixation of objects to bone.

A variety of techniques are available for affixing objects, such as soft tissue, to bone. The oldest technique for affixing soft tissue to bone is to pass a thread through the bone and sew the tissue down to the bone. Many sizes, shapes and types of suture and needles are available to accomplish this task. Today, this method is still used for repair of tendons and ligaments in the hands of older osteoarthritic patients, although passing sutures through bone is generally difficult and tedious.

Venable et al. (1937), *Annals Surg.*, Vol. 105, pp. 917-38, describes reactions of bone to metals, and recommends using Vitalium, an iron free and body fluid resistant alloy, for internal fixation devices, and particularly for screws. Prior to this publication, soft tissue repairs generally had been accomplished with string (suture), silver wires, or ivory pegs. Following publication of Venable et al., screws came into common surgical use, at first for repairing bone fractures, and later for attaching soft tissue to bone.

Vitalium staples were described for use in soft tissue repairs about 1940. Later many different types and styles of staple were suggested, including, for example, staples having four legs, or barbs in the legs, or various configurations of crossmember, including dentitions.

Metal implants, including implants made of stainless steel, are subject in time to corrosion and consequent loss of structure. Moreover, the presence of metal in an anatomical site can interfere with certain imaging diagnostic or therapeutic treatments near the site, such as magnetic resonance imaging; and where the use of such imaging is indicated, any metal implants may first have to be surgically removed. Patient sensitivity to free nickel ions in stainless steel implants has fueled a growing controversy regarding the use of materials containing high quantities of nickel, including nickel-titanium alloys such as Nitinol.

Generally, the tissues react to metal screws and staples as foreign bodies, and these objects can be expected to loosen in time as a result of rejection of them by the tissues. A loosened screw or staple can be expelled from the bone, and can lodge in a joint, where it can cause damage to articulating surfaces. In a significant proportion of cases, where the screw or staple has been expelled or has loosened, it must be removed in a subsequent surgical procedure.

Since the development of the stainless steel screw and staple, many small improvements have been made for fixing soft tissue to bone. In one improvement, described for example in Daniel et al., Chapter 8, In: Jackson et al. (1987), *The Anterior Cruciate Deficient Knee*, C. V. Mosby, pp. 114-126, a circular plastic washer with spikes on its undersurface is installed beneath the screw head to provide fixation without crushing the tissue, and toothed washer devices have been commercialized by, for example, A. O. Synthes, Switzerland. This method was until recently widely accepted as the best method of fixating soft tissue to bone, except in shoulder repair where sutures passed through holes drilled through the glenoid margin and through the edge of the glenoid capsule continue to be used for approximating the capsule to the glenohumeral rim, generally as described in Bankart (1983), *British Jour. Surg.*, Vol. 26, pp. 23-39. Rowe et al. (1984), *Jour. Bone Joint Surg.*, Vol. 66A, pp. 159-68, for example, describes using a Bankart procedure and in all instances avoiding the use of metal implants such as staples and screws in the vicinity of the shoulder joint.

Necrosis of the soft tissue can result if the tissue is too tightly clamped by screws or staples, and several attempts have been made recently to improve the soft tissue fixation by screws and staples to overcome this problem, such as by using toothed washers, as described above, or by using stand-off devices to prevent crushing the soft tissue. On the other hand, if the soft tissue is too loosely fixed to the bone, the holding power of the tissue attachment is inadequate to facilitate effective soft tissue reattachment to bone. Because it is almost impossible to adjust the compression exerted by screws and staples on soft tissue, these devices are not fully satisfactory for soft tissue repair. The surgeon's fondness for suture in soft tissue repairs has never diminished, owing primarily to the fact that, by setting the tension of the suture, the surgeon can fix the soft tissue to the bone as tightly as is appropriate in the particular case and according to the surgeon's practice.

Somers et al. (1985), U.S. Pat. No. 4,632,100, describes a cylindrical suture anchor having a drill formed at one end and flights of screw threads at the other end. The device combines a drill point for penetrating the hard outer cortical bone with a screw for fixing the device into the hard bone, providing for drilling the bone and installing the anchor in one operation. A Somers et al. device, marketed as STATAK TM by Zimmer, Inc. (Warsaw, Ind.), is screwed into a 4.5 mm diameter bone hole, and is intended to be countersunk into the cancellous bone to a depth up to 18 mm, and so it is not ideal for use in smaller joints. The relatively large size and the comparatively high cost of the device, and its requirement for a large hole in the bone, may be deterrent to its use, and it has not been well received.

Goble et al. (1986), U.S. Pat. No. 4,738,255 describes a suture rivet that can be inserted into and locked in place in a performed hole in bone. The initial pilot hole is cut using a drill having scissoring blades, so that the resulting hole is flared or skirted, having a greater diameter deeper within the bone than at the entry to the bone surface. The anchor itself includes a rivet and a slotted ring. The slotted ring, which passes the smaller entry hole, is inserted within the bone, and then the rivet is passed into the hole and through the ring, fracturing the ring at the point where it is slotted and flaring the ring so that it cannot pass out through the entry hole, locking the assembly into the bone hole. The Goble et al. apparatus is relatively complicated, and the scissoring device can be unreliable in use.

Gatturna et al. (1987), U.S. Pat. No. 4,898,156, describes a suture anchor assembly consisting of a titanium body affixed to a nickel titanium arc of wire. The nickel titanium arc is of pseudoelastic nitinol, which can be strained such that the arc will straighten completely, allowing the assembly to be placed into a predrilled bone hole. The titanium body has a drilled cross hole which allows a suture to be attached to the body prior to insertion in the bone hole. The installation tool consists of coaxially disposed cannulae, which constrain the nitinol arc prior to insertion.

Nicholson et al. (1987), U.S. Pat. No. 4,899,743, describes a suture anchor installation tool that holds the Gatturna et al. suture anchor so that the nitinol arc is unconstrained, essentially hanging outside the installation tool. Prior to insertion the assembly resembles a one barbed fish hook in the end of a small spear. A hole is predrilled in the bone, and the anchor assembly is gently pushed into the predrilled hole, allowing the nickel titanium arc to slide down the side of the hole. A Gatturna et al. anchor and Nicholson et al. installation tool, commercialized by Mitek Surgical Products, Inc., beginning in late 1989, have become a preferred method of anchoring soft tissue to bone; many were sold in the first year following FDA approval. The device can be effective in aiding in soft tissue reattachment, and has an advantage in requiring a relatively narrow hole in the bone.

However, the Gatturna et al. anchor is set by applying traction to the suture, and so the device does not lend itself to use as a rivet, in which no suture would be required to anchor the tissue. Moreover, use of the device is contraindicated in very soft, cancellous bone, as is typical of bone in many joints, so the device is not optimal for such procedures as rotator cuff repair, osteoarthritis joint reconstruction, and the like. When the Gatturna et al. anchor is deployed in an arthroscopic application using the Nicholson et al. installation tool, the protruding barb can engage sensitive tissues during placement and cause damage to the tissues.

Hayhurst (1988), U.S. Pat. No. 4,741,330, and international patent Publication No. WO 89/10096 describes a suture anchor including a generally bullet-shaped resilient plastic member having a rounded convex base from which legs extend. The legs, which are provided with outward-pointing barbs on their outer surface, diverge outwardly when the member is in a relaxed state. The member is compressed and inserted into a predrilled bone hole, and then allowed to relax, so that its resilience is said to urge the legs outward against the bone hole wall. The anchor supposed to be set by applying tension to the suture, causing the edges of the legs and the surface barbs to dig into the bone. A similar device, marketed by Acufex Microsurgical, is driven into the bone hole apparently into the cancellous bone, and is then set by pressing a spreader downward between the legs while pulling upward on the suture to force open the legs.

Bays et al. (1990), U.S. Pat. No. 4,924,865, describes a bioabsorbable tack for joining severed or torn soft tissues, such as cartilage. The stem of the generally T-shaped tack is hollow and covered with barbs on its outer surface. The tack is implanted by passing the stem through a hollow cylindrical applicator and passing a needle through the axial bore in the stem, then driving the needle, tack and applicator through the tissues to the desired depth, and then withdrawing the needle and applicator, leaving the tack in place.

SUMMARY OF THE INVENTION

In general, in one aspect, the invention features a bone fastener, including an expandable sleeve having an axial bore and a pin forcibly insertible into the axial bore, the expandable sleeve being configured to be insertible into a bore drilled in bone, at least a portion of the pin having an outer diameter greater than the inner diameter of at least a portion of the axial bore.

The invention provides for fixing either a suture fastener or a rivet within a narrow, shallow hole predrilled in the bone. The fastener is emplaced by inserting the sleeve into a predrilled hole in the bone, and then forcing the pin into the axial bore, so that the wider portion of the pin presses outward against and expands the narrower portion of the sleeve, causing the sleeve to forcibly contact the walls of the bone hole and fixing the pin and sleeve firmly in place within the hole.

In some preferred embodiments, the pin includes a head for retaining an object to be attached to the bone; the sleeve has a generally cylindrical configuration; the outer surface of the sleeve when the sleeve is expanded conforms to irregularities in the bone hole wall; the outer surface of the sleeve is provided with a plurality of protrusions; the outer surface of the sleeve is provided with at least one annular ridge, and preferably the outer surface of the sleeve is threaded; the sleeve is made of a thermoplastic material capable of expanding when pressed outwardly by the pin; the thermoplastic material is capable of conforming under pressure with irregularities in the bone hole wall; the thermoplastic material is preferably a high density biocompatible polymer such as a high density polyethylene, or a high density polypropylene; the pin includes an axial bore; the pin is made of a high impact material, preferably a high impact biocompatible polymer such as for example a polycarbonate or a polysulfone or an acetal resin such as DuPont Delrin TM.

In another general aspect, the invention features a method for establishing a fastener in a predrilled hole in bone, including steps of inserting into the hole an expandable sleeve having an axial bore, and forcing into the axial bore a pin, at least a portion of the pin having a diameter greater than that of at least a portion of the axial bore, so that as the pin is forced into the axial bore the wider portion of the pin presses outward against the narrower portion of the sleeve, causing the sleeve to expand against the walls of the hole and fixing the pin and sleeve firmly in place within the hole.

Preferably, during the step of forcing the pin into the axial bore a counter force is imposed on the expandable sleeve in a direction about opposite from, and in a magnitude about equal to, the force imposed on the pin, to minimize any net force toward or away from the bone during the expansion of the sleeve against the walls of the hole.

In another general aspect, the invention features apparatus for emplacement of a fastener according to the invention including a holder for holding the expandable sleeve in position within the predrilled hole in the bone, and a plunger moveable in relation to the holder for forcing the pin into the bore, so that the pin can be forced into the axial bore without imposing substantial net forces toward or away from the bone.

In preferred embodiments, the holder includes a generally cylindrically shaped hollow body having a front and a rear end, the body being severably attached near its front end to the rear end of the expandable sleeve, means moveable within the body for forcing the pin into the expandable sleeve, and means for severing the attachment between the holder and the expandable sleeve after the pin has been forced into the expandable sleeve; the severable attachment of the holder body to the expandable sleeve includes an annular portion connecting the front end of the body to the rear end of the expandable sleeve; the severable attachment includes a web or a plurality of spoke members connecting the front end of the body to the rear end of the sleeve; the severable attachment is more resistant to being severed by forces urging the holder body in a frontward or rearward direction in relation to the sleeve than in a direction perpendicular to the front-to-rear axis; the severable attachment is a removable couple, preferably a rotationally removable couple such as a threaded or bayonet attachment; the pin forcing means includes a rod that can be moved frontwardly and rearwardly with respect to the holder body and that when moved frontwardly can abut the rear end of the pin to force it into the axial bore in the expandable sleeve; the attachment severing means includes a cutting edge such as a cylindrical blade having an annular cutting edge; the severing means is activatable independently of the plunger; the severing means includes heating means such as, for example, a cauterization loop, for softening the attachment.

The rearward portion of the sleeve can be configured to provide a "head", so that the sleeve can be passed first through the object to be attached to the bone and then into the predrilled bone hole, and then fixed by forcible insertion of the pin, for attachment of objects such as, for example, bone plates, or for attachment of soft tissues, without use of sutures. A part of the sleeve between the bone-engaging portion and the head can be smooth, providing a "standoff" beneath the head when the fastener is fixed, and the sleeve can be further configured at a selected distance frontward from the head to provide a "stop" for engaging the edge of the bone hole and limiting the depth to which the sleeve can be passed into the bone, so that the standoff can have a selected height above the bone.

In preferred embodiments at least a part of the rearward portion of the sleeve is configured to form a head; more preferably the head is configured as a flange; the flange has a circular margin; the sleeve is smooth over a part of its length frontward of the head; at least a part of the sleeve at a distance frontward from the rearward end of the sleeve is expanded to form a stop.

In some sleeve configurations a sleeve having threaded outer surface can have an outer diameter at its widest point that is somewhat greater than the inner diameter of the bone hole; so that the sleeve can be turned into the hole rather than merely slipped into the hole. In such configurations the screw threads serve to tap the hole to some degree as the sleeve is turned into the hole. Such an arrangement can provide placement of the sleeve to a more precise depth within the bone, and, where the fastener is adapted to have a head, such an arrangement can provide for a more precise degree of compression of the tissue or other object to be fastened between the head and the bone surface during placement of the sleeve. Once the sleeve has been placed to the desired depth, or the object has been compressed to the desired degree, the screw threads can hold the sleeve in place temporarily. Then the fastener is fixed in place by forcing the pin into the axial bore of the sleeve. As in embodiments in which the unexpanded sleeve slips without substantial resistance into the bore hole, fixation is effected in self-tapping screw thread embodiments by expansion of the sleeve in the bore hole, and deformation of the outer portions of the sleeve and conformation of the outer surface of the sleeve with irregularities in the bone hole wall. In self-tapping embodiments, a portion of the screw threads can be sufficiently hard to provide for cutting or abrading the bone while the sleeve is turned into the hole.

In other preferred embodiments the outer surface of the sleeve is configured to form screw threads having an outer diameter slightly larger than the inner diameter of the bone hole; a portion of the screw threads is sufficiently hard to tap the bone hole to a degree as the unexpanded sleeve is turned into the bone hole.

DESCRIPTION OF PREFERRED EMBODIMENTS

DRAWINGS

FIGS. 1.1–1.4 are a series of diagrams, drawn in sectional views along the long axis, showing emplacement into bone of a bone fastener according to the invention.

FIGS. 2.1 and 2.2 are diagrams, drawn in sectional views as in FIGS. 1.1 and 1.4, showing emplacement into bone of a bone fastener having a head according to the invention.

FIGS. 3.1 and 3.2 are diagrams, drawn in sectional view as in FIGS. 1.1 and 1.3, showing apparatus for effecting emplacement of a fastener according to the invention.

FIG. 4.1 is a diagram, drawn in sectional view as in FIG. 1.1, of an alternative bone fastener according to the invention having the form of a self-tapping screw.

FIGS. 4.2 and 4.3 are diagrams, drawn in sectional view as in FIGS. 1.2 and 1.3, showing alternative severable attachment for use in a headed fastener.

FIGS. 8.1 and 8.2, and 9.1 and 9.2 are diagrammatic representations in transverse sectional view, showing alternative severable attachment of the fastener sleeve and the holder according to the invention.

FIGS. 10.1, 10.2 are drawings in elevational and axial views showing a preferred expandable fastener sleeve and holder according to the invention.

FIG. 10.3 is a section thru the axis of the fastener sleeve and holder of FIG. 10.1, and FIG. 10.4 is a detail of the portion indicated at D in FIG. 10.3.

FIGS. 11.1, 11.2 are drawings in elevational and axial views showing a further preferred expandable fastener sleeve and holder according to the invention.

FIG. 11.3 is a section thru the axis of the fastener sleeve and holder of FIG. 11.1, and FIG. 11.4 is a detail of the portion indicated at D in FIG. 11.3.

FIGS. 12.1, 12.2 are drawings in elevational and axial views showing a preferred headed pin insertible into the axial bore of an expandable fastener sleeve to form a rivet fastener according to the invention.

FIG. 12.3 is a section thru the axis of the headed pin of FIG. 12.1.

STRUCTURE

The bone fastener according to the invention generally includes a pin and an expandable sleeve having an axial bore. In its unexpanded state the expandable sleeve can be inserted into a predrilled hole in the bone without substantial resistance between the wall of the hole and outer portions of the sleeve. The diameter of at least a portion of the pin is greater than that of at least a portion of the axial bore, so that when the pin is forced into the axial bore, the wider portion of the pin presses outward against the narrower portion of the sleeve, causing the sleeve to expand against the wall of the hole, fixing the pin within the sleeve firmly within the hole and providing the fastener. The pin or the expandable sleeve, or both of them, can be adapted to provide a fastener for a suture or to provide a rivet.

The description that follows illustrates, by way of example, embodiments of suture fasteners and rivets according to the invention.

SUTURE FASTENER

Figure 14:
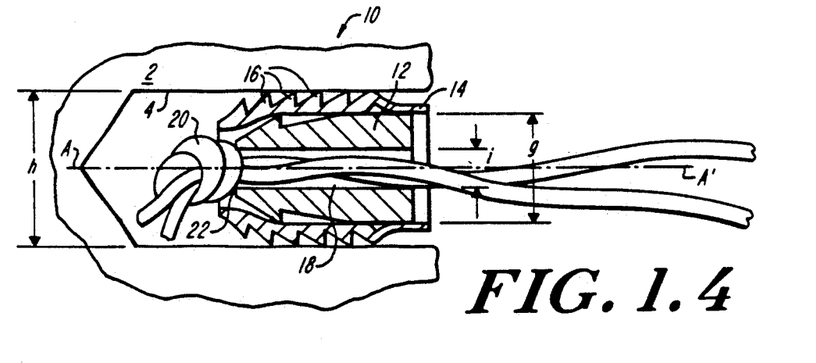
Figure 21:
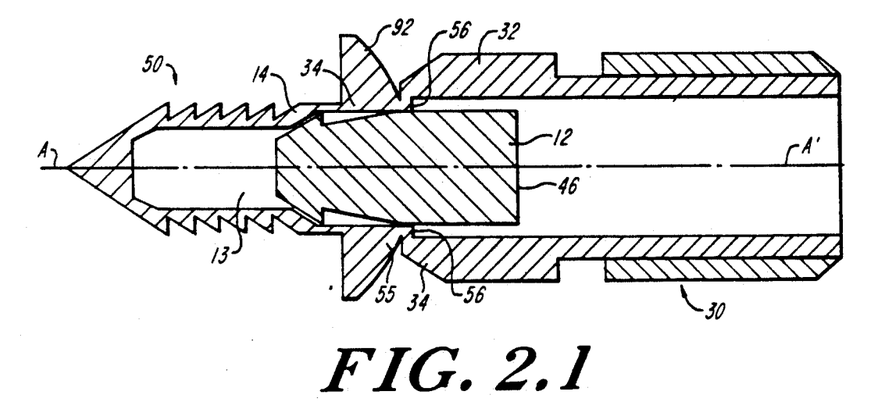

FIG. 1.4 illustrates in diagrammatic sectional view a suture fastener 10 emplaced in a predrilled hole in bone according to the invention. Pin 12 has been forced into expandable sleeve 14, expanding sleeve 14 to press outer portions 16 against wall 4 of the hole in bone 2. Suture 20, which can be, for example, a standard braided polyester (Dacron) suture, is knotted against front end 22 of pin 12 and passes through axial bore 18 in pin 12 out of the fastener, where it can be used to attach soft tissue to the bone at the fixation site.

Figure 7:
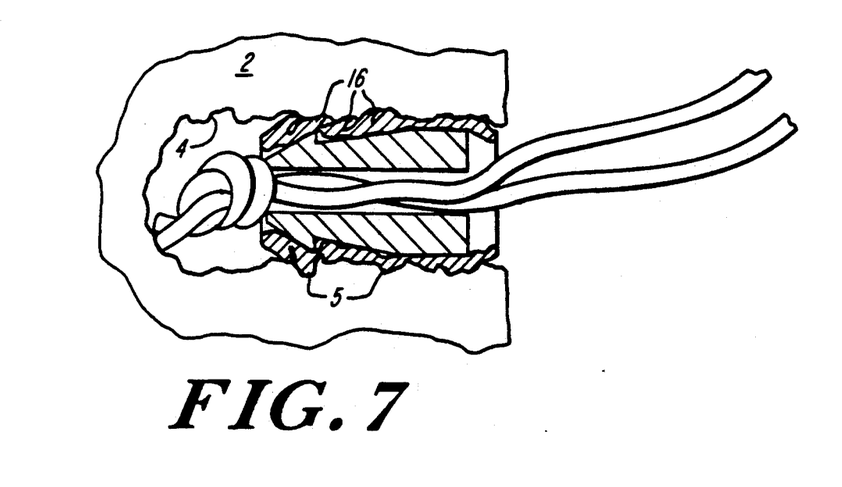
FIG. 7 is a drawing as in FIG. 1.4, but in a less diagrammatic representation, showing deformation of the outer portion of the sleeve within irregularities in the bone hole wall resulting from forcible expansion of the sleeve within the bone hole.

In practice, sleeve outer portions 16 will have become distorted as they conform to irregularities in the bone hole wall 4 under the outward pressure caused by the intrusion of the pin 12 into the axial bore of the sleeve. Sleeve 14 may, if the expansion is great enough, rupture; a ruptured sleeve may provide sufficient fixation, provided that the pin 12 is firmly held within. For clarity of presentation in the Figs., except in FIG. 7, the expanded sleeve 14 is shown undistorted; and the bone hole is shown as being larger relative to the width of the expanded sleeve than would be desirable for firm fixation of the fastener. FIG. 7 shows a less diagrammatic representation of the appearance in section of a fastener 10 emplaced in a hole in cortical bone 2 whose diameter is somewhat less than the diameter of the unexpanded sleeve. As FIG. 7 illustrates, the outer surface of the sleeve 16 is so deformed as it conforms to irregularities 5 in bone hole wall 4 that the threaded form of the outer surface of the unexpanded sleeve is practically unrecognizable. The shape assumed by the expanded sleeve in any particular bone hole depends in part upon characteristics of the particular bone hole and of the bone matter itself.

The expandable sleeve 14 is preferably constructed of a biocompatible implant material that is sufficiently deformable that, when expanded within the bone hole, will conform to a substantial degree with irregularities in the bone hole wall, and the pin 12 is preferably constructed of a relatively hard biocompatible implant material such that the pin can cause the sleeve to expand and to deform against and conform to irregularities in the bone hole wall. Suitable sleeve materials include, for example, an implant grade high density polyethylene, and suitable pin materials include, for example, an implant grade high impact polymer such as a Delrin 100 acetal resin or a polycarbonate. The sleeve or the pin can be made using a combination of materials, provided that they provide for an appropriate combination of biocompatibility, and (in the sleeve) deformability and conformability relative to the bone, and (in the pin) incompressibility or hardness relative to the sleeve and to the means for forcing the pin into the sleeve axial bore, and sufficient rigidity to hold the suture or the object to be attached to the bone.

Figure 11:
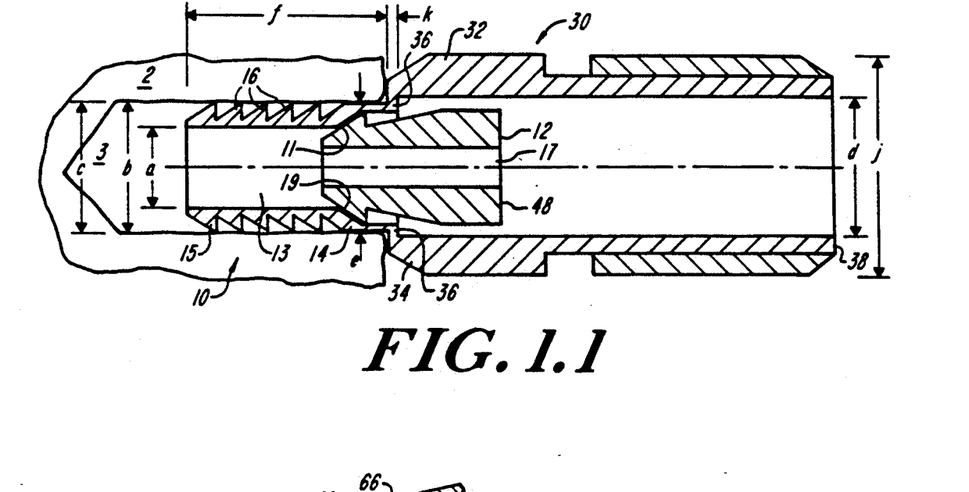
Figure 12:
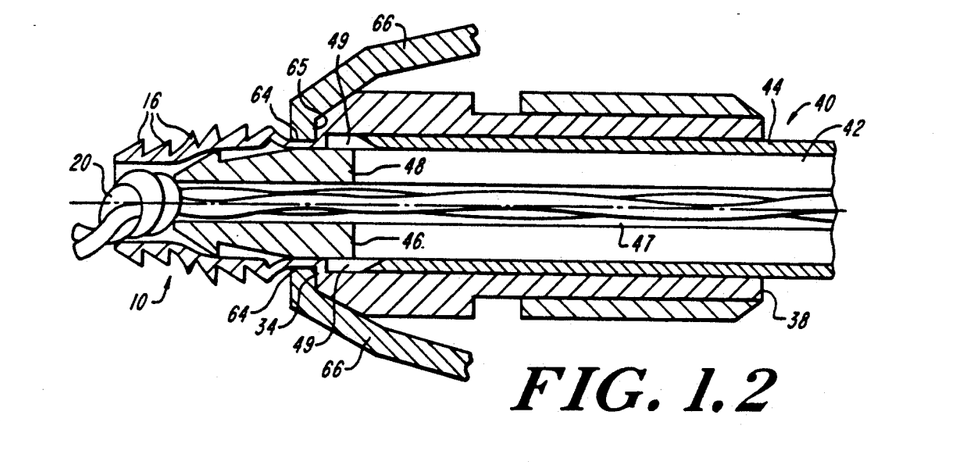
Figure 13:
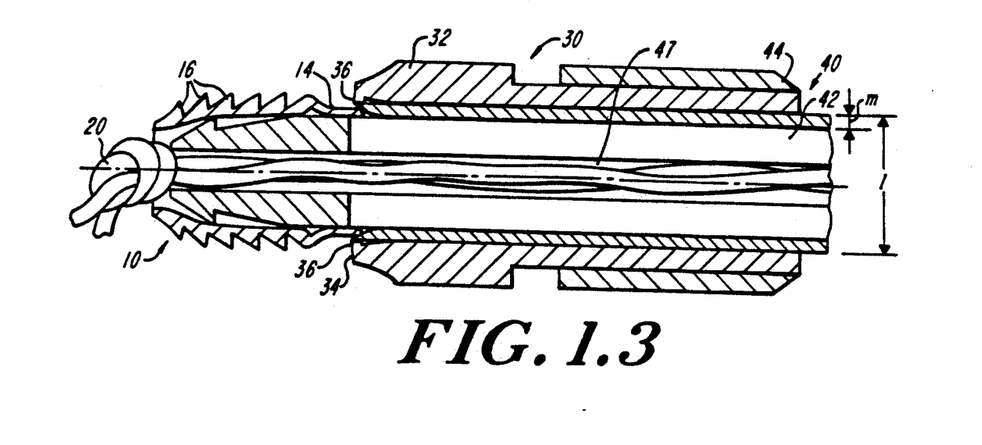

FIGS. 1.1–1.3 show emplacement of fastener 10 within a hole 3 previously drilled in the bone 2 at the fixation site, using preferred emplacement apparatus 30, which is adapted to provide for firm fixation of the fastener without imposing substantial forces upon the bone itself in directions toward or away from the bone.

Referring now to FIG. 1.1, expandable sleeve 14, having axial bore 13 and outer surface 15, is shown in an unexpanded state, in which the axial bore has a diameter a and the outer surface has a diameter b at its widest point or points. Diameter b is no greater than the diameter c of the bone hole 3, so that sleeve in its unexpanded state passes into hole 3 substantially without resistance.

Emplacement apparatus 30 includes a generally cylindrical holder body 32 having an inside diameter d greater than the outside diameter e of the rear end 17 of sleeve 14. Sleeve rear end 17 is attached to holder body front end 34 annular attachment portion 36.

Pin 12 is shown in FIG. 1.1. poised with its beveled front portion 11 close to similarly beveled rear portion 19 of the inner surface of the expandable sleeve 14. As FIG. 1.2 shows, a plunger 40, having a rod 42 surrounded by a cylindrical blade 44 is introduced by way of the rear end 38 of the holder body 32, and the plunger is urged forward, so that its front end 46 abuts rear end 48 of pin 12. Then plunger 40 is further urged frontward, pressing pin 12 before it into axial sleeve bore 13. FIGS. 1.2 and 1.3 show the progress of expansion of sleeve 14 as beveled front portion 11 of pin 12 presses outward against the inner surface of sleeve 14 as pin 12 is forced frontward to its full extent, as shown in FIG. 1.3.

As pin 12 approaches its full frontward position, cutting edge 49 of cylindrical blade 44 approaches, then meets, and then passes through annular attachment portion 36, severing the sleeve 14 from the holder body 32, and thereby freeing the fully expanded and firmly fixed fastener 10 from the emplacement apparatus 30. The emplacement apparatus 30 is then withdrawn, leaving the fastener and the suture in place at the fixation site in the bone.

Sleeve outer surface 15 has protrusions, shown in FIGS. 1.1–1.4 as a plurality of annular ridges 16, for engaging irregularities in the bone hole wall 4 as the sleeve deforms and conforms to the bone hole wall as it is forcibly expanded within bone hole 3.

FIGS. 11.1–11.4 show a more preferred emplacement apparatus, generally similar to fastener assembly 30 in FIGS. 1.1–1.3, but differing in some particulars. Fastener assembly 230 includes a holder body 232 severably attached to an expandable sleeve 214; the latter has an axial bore 213 and an outer surface 215. Expandable sleeve 214 (see detail at FIG. 11.4) is shown in an unexpanded state, in which the outer diameter b of the outer surface 215 is no greater than the diameter of the bone hole, so that the sleeve passes into the bone hole substantially without resistance, as described above with reference to FIG. 1.1. Generally cylindrical holder body 232 has an inside diameter d greater than the outside diameter of the rear end 217 of sleeve 214. Expandable sleeve rear end 217 is joined to holder body front end 234 by annular attachment portion 236. Expansion of the sleeve 214 within the bone hole is effected by pressing into the axial sleeve bore 213 a pin (not shown in FIGS. 11.1–11.4) having an outer diameter greater than the diameter a of the axial sleeve bore.

For fixation in, for example, the humoral head or the glenoid process, the diameter b of a suitable unexpanded sleeve is about 3.5 mm, and the length of the engagement portion of the sleeve (that is, the portion of the sleeve that, when fully emplaced, contacts the bone hole wall) is about 10 mm.

FIGS. 10.1-10.4 show still another more preferred emplacement apparatus, like that of FIGS. 11.1-11.4 in many particulars, but adapted for use with a pin having a head, to provide a rivet fastener. Such a pin 412 having a head 414 is shown by way of example in, and described below with reference to, FIGS. 12.1-12.3. Like fastener assembly 230, rivet fastener assembly 330 includes a holder body 332 severably attached to an expandable sleeve 314 (shown in the unexpanded state in the Figs.); the latter has an axial bore 313 and an outer surface 315. Generally cylindrical holder body 332 has an inside diameter d substantially greater than the outside diameter of the rear end 317 of sleeve 314, and great enough to accommodate the diameter e of head 414 of pin 412. Expandable sleeve rear end 317 is joined to holder body front end 334 by annular attachment portion 336, which is provided with a circular undercut 338 to facilitate separation of the sleeve from the cylindrical holder body, at the completion of the emplacement of the fastener in the bone, as described further below.

RIVET FASTENER

The expandable sleeve, as described above with respect to FIGS. 1.1-1.4, can be adapted to form a "rivet" for directly riveting soft tissue, or an object such as a bone plate, to the bone at the fixation site. FIGS. 2.1 and 2.2 show an example of such a rivet, in which the rear end of the sleeve is configured to form a head.

Figure 22:
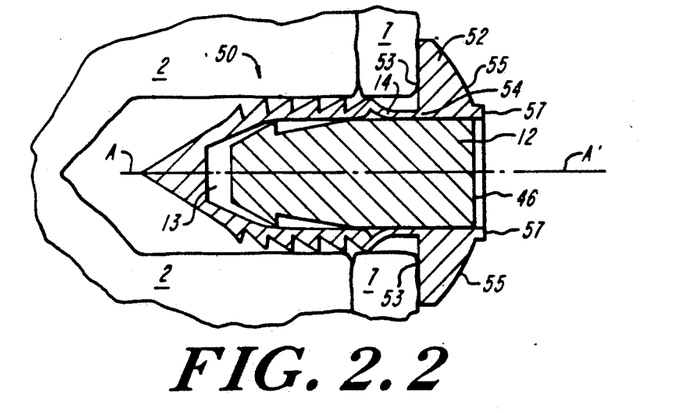

Referring now to FIG. 2.2, showing the rivet fastener 50 fixed in a predrilled bone hole, the rivet head is formed as a flange 52 at the rear end 54 of expandable sleeve 14. The front surface 53 of the flange 52 is generally planar and perpendicular to the axis A—A' of the sleeve, and the rear surface 55 is contoured to provide a smooth, generally dome-shaped head, thinner near the margin than toward the center.

The rivet is preferably emplaced in generally the same fashion as is the suture fastener, described above with reference to FIGS. 1.1-1.4, and preferably is provided with similar emplacement apparatus 30 and is installed using similar plunger 40, as shown in FIG. 2.1. Here, the sleeve is first passed through the object (for example, soft tissue such as a ligament or a bone prosthesis such as a plate) to be attached to the bone, and then is inserted into the bone hole far enough to provide an appropriate compression of the attached object onto the bone surface. Preferably the front end of a sleeve adapted for use as a rivet for attaching soft tissue to bone is contoured to pass easily through the tissue, and the axial bore does not pass through the front end of the sleeve. A generally conical sleeve front end 51 is suitable for retrieving and passing through soft tissue such as a ligament. The rear surface 55 of the flange 52 is attached to holder body front end 34 by annular attachment portion 56. As described above with reference to FIGS. 1.2 and 1.3, as plunger 40 is urged forontward, it presses pin 12 before it into axial sleeve bore 13, expanding sleeve 14 as pin 12 is forced frontward. As pin 12 approaches its final position, at which its rear surface 46 is approximately flush with the rearmost part 57 of the rear surface of flange 52, cutting edge 48 of cylindrical blade 44 approaches, then meets, and then passes through annular attachment portion 56, severing the sleeve 14 from the holder body 32, and thereby freeing the fully expanded and firmly fixed rivet fastener 50 from the emplacement apparatus 30. The emplacement apparatus is then withdrawn, leaving the rivet fastener in place at the fixation site in the bone, compressing the attached object 7 between the front surface of the head and the surface of the bone 2.

Figure 42:
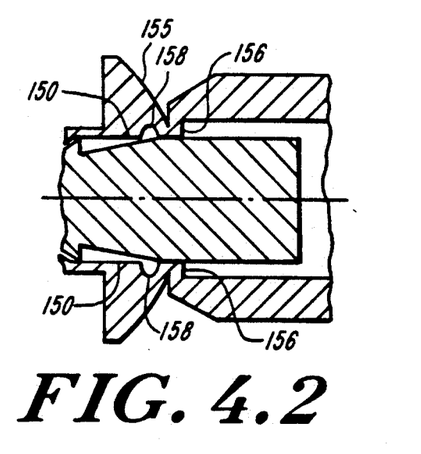
Figure 43:
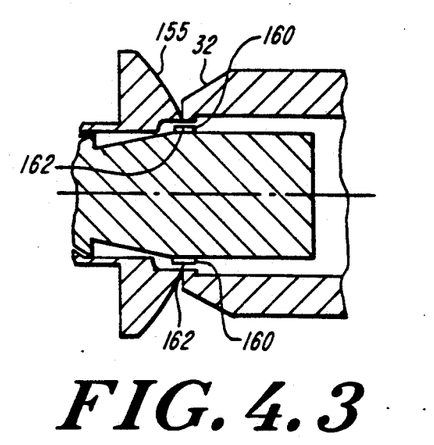
Figure 81:
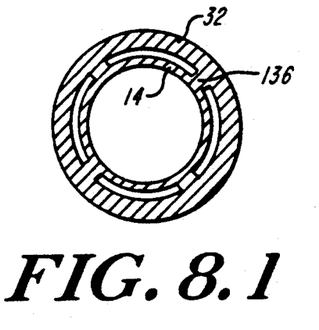
Figure 82:
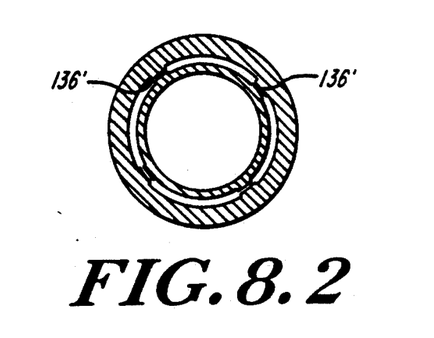
Figure 91:
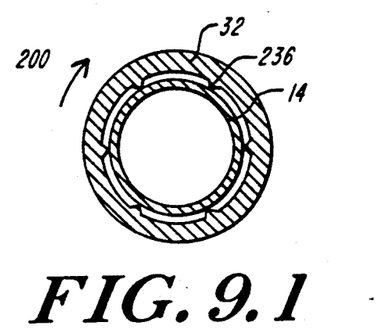
Figure 92:
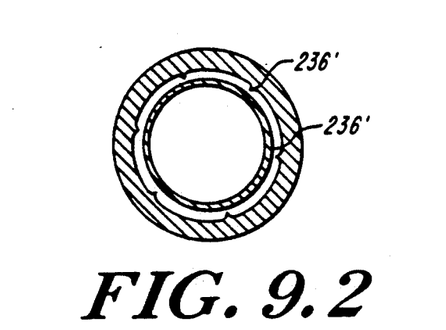

As will appear from FIG. 2.2, the rear head surface 55 can be left with a small rim of connective material following severing as described above. Alternate configuration for the head and severable attachment is shown by way of example in FIGS. 4.2 and 4.3. As shown in FIG. 4.3, the inner surface 150 of the sleeve can be provided with annular excavation 158 just frontward of the severable attachment 156. The excavation is formed sufficiently deeply into the material of the head so that when the cutting or shearing means passes through, an annular fragment 160 is cut free of both the head surface 155 and the sleeve 32, and any remaining connection 162 between the head surface and the sleeve is so thin that it provides little resistance to the simply pulling the sleeve away from the fixed fastener.

As noted above, the sleeve is fabricated from a relatively deformable material, while the pin is of a harder material, so that urging the pin into the axial bore of the sleeve deforms the sleeve outward against the wall of the bone hole. We have discovered that a stronger and more durable rivet fastener can be made according to the invention by using a pin having a head, rather than by forming the head as a flange at the rear end of the sleeve. The head of the resulting rivet is thus of the stronger pin material, and the neck portion of the rivet is supported by part of the barrel of the pin.

Such a headed pin is shown by way of example in FIGS. 12.1-12.2, and a preferred fastener assembly for use with a headed pin is shown by way of example in, and described above with reference to, FIGS. 10.1-10.4. Referring now to FIGS. 12.1-12.3, pin 412 has a generally cylindrical barrel 416 traversed by an axial bore 418, provided at its rear end with a head 414 and at its front end with a beveled portion 411.

Figure 5:
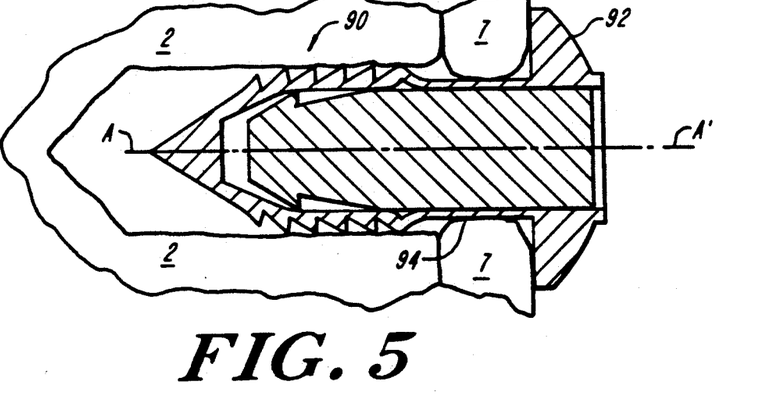
FIG. 5 is a diagram, drawn in sectional view as in FIG. 2.2, showing in place a bone fastener having a head and a standoff according to the invention.
Figure 6:
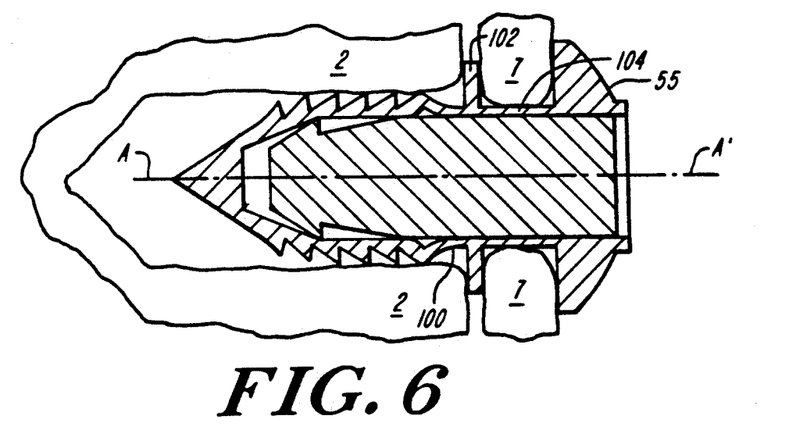
FIG. 6 is a diagram, drawn in sectional view as in FIG. 5, showing in place an alternative bone fastener having a head and a stop, providing a specified standoff according to the invention.

The expandable sleeve 314 passes without resistance into the bone hole, as described above generally; for emplacement as a bone rivet, the sleeve is positioned within the bone hole so that an externally smooth neck portion 304 projects above the bone surface, to provide a standoff between the rivet head and the bone surface, generally as described in more detail below with reference to FIGS. 5 and 6. An annular ridge 302 can retain a tissue-locking washer, preventing loss of the washer during insertion of the sleeve into the bone hole.

The outer diameter r of the cylindrical barrel 414 is about the same as, or slightly smaller than, the inner diameter s of the neck portion 304 of the expandable sleeve 314; and the diameter r is larger than the inner diameter a of the axial bore 313, so that as the pin 412 is forced into the axial bore 313, it passes without substantial resistance through the neck portion, but causes the bone-engaging portion to expand outwardly against the wall of the bone hole. Thus, as pin 412 is urged frontward the beveled portion 411 presses outward against the inner surface of the bone-engaging portion of the sleeve, beginning at the beveled portion 319 of the interior of the sleeve, as described generally above with reference to FIG. 1.1-1.3. As the front surface 453 of the pin head 414 contacts the rear surface of the annular attachment portion 336 between the rear of the neck portion of the sleeve and the front portion of the holder body, the progress of the pin within the sleeve is stopped, and further frontward urging of the pin causes a failure of the annular attachment portion 336, effecting separation of the fully installed fastener from the holder body. Then the emplacement apparatus can be withdrawn from the site. Preferably, the head is provided with an abrupt front edge 454, to effect a shearing action; and the annular attachment portion 336 preferably is provided with a circular undercut 338 to further improve the precision of the separation.

Thus emplaced, the resulting rivet fastener is anchored firmly in place within the bone hole by the intimate contact of the deformed surface of the bone-engaging portion 315 of the expanded sleeve 314 with the bone hole wall; the shaft 416 of the pin 412 within the axial bore 313 holds the expanded sleeve tightly against the bone wall. The neck portion 304 of the sleeve stands above the bone surface, supported by the more rearward portion of the pin shaft 416 within. The head 414 of the pin 412 abuts the part of the annular attachment 336 that remains at the rear end of the sleeve following separation from the holder body, so that the material to be fastened by the rivet is confined about the supported neck portion 304 of the sleeve, between the bone surface and the front-facing surface 453 of the pin head.

INSERTION TOOL

Figure 31:
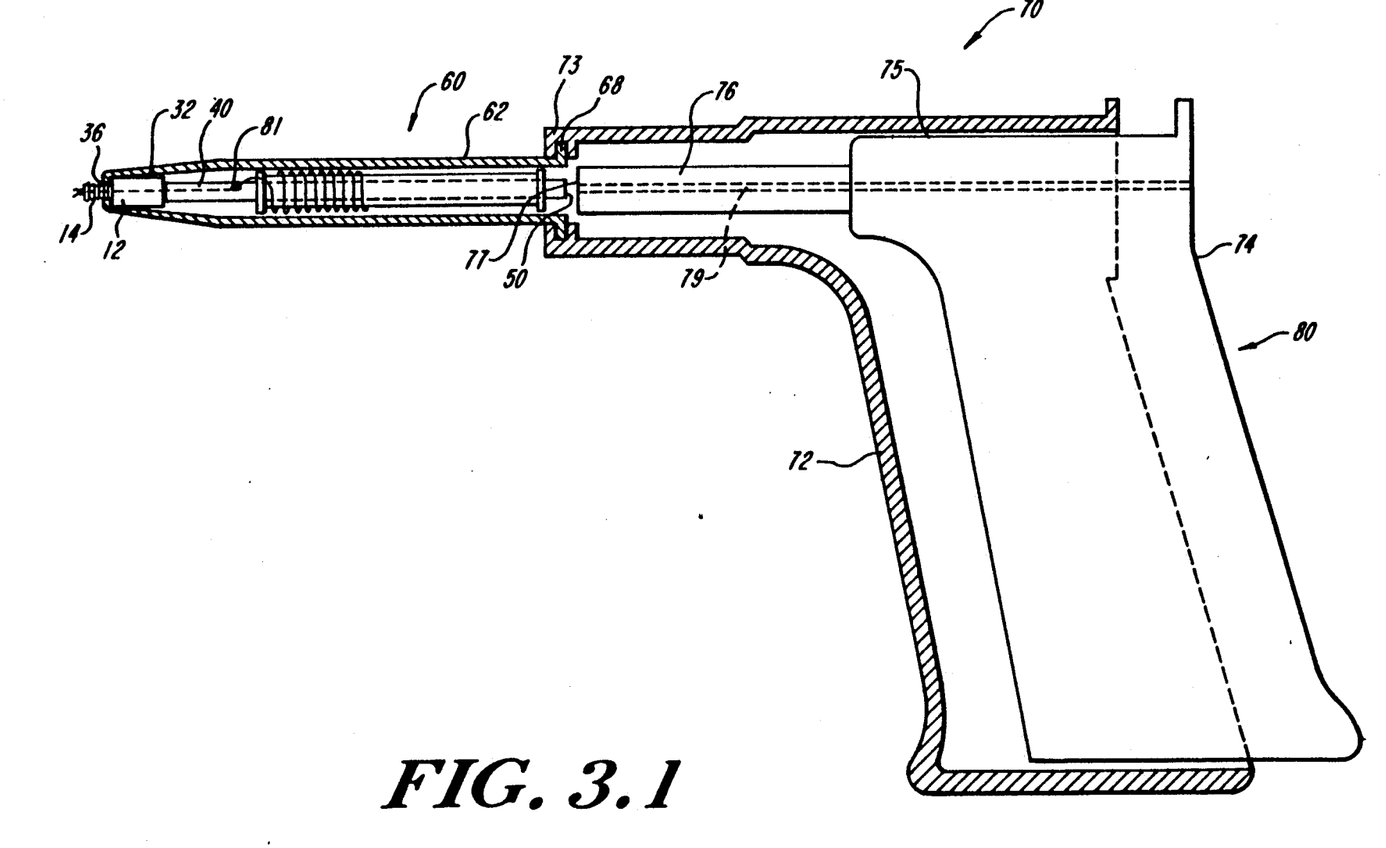
Figure 32:
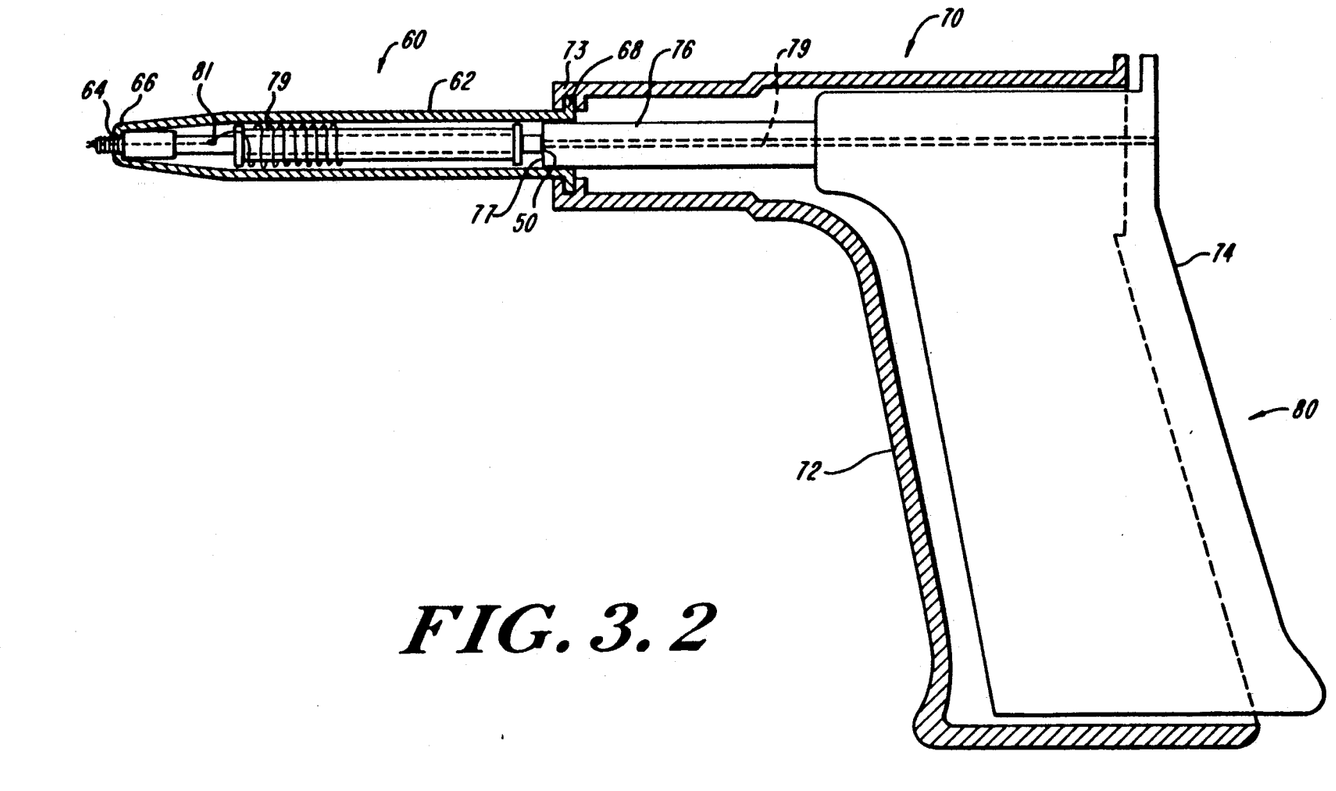

A preferred emplacement apparatus retains the pre-engaged fastener assembly prior to activation. The apparatus includes means for pressing the pin into the sleeve and then separating the base from the assembly. The fastener assembly can be a disposable cartridge 60, as shown for example in the suture fastener assembly of FIGS. 3.1 and 3.2. The cartridge contains the fastener assembly, the pin and a means of easily attaching the disposable cartridge to the apparatus.

In more detail, with reference to FIGS. 3.1 and 3.2, a fastener assembly 60 includes disposable cartridge 62 containing emplacement apparatus 30, including holder body 32 attached by annular attachment portion 36 to expandable sleeve 14 as described above with reference to FIG. 1.1, preloaded with plunger 40 and pin 12, poised with its beveled portion 11 close to the beveled portion 19 of the sleeve 14, as shown in FIG. 1.1; and provided with a suture 20, passing through the axial bore 18 of the pin and through an axial bore 47 of the plunger and knotted against the front end 22 of the pin. The knot 20 is fully contained within the sleeve prior to emplacement of the fastener in the bone hole, so that it cannot interfere with the insertion of the fastener into the hole.

An axial bore 64 in nose 66 of cartridge 62 is dimensioned to closely fit the outside diameter of the rear portion of the sleeve 14, as shown more clearly in FIG. 1.2, and, for clarity of presentation, excluded from other FIGS. The holder body with attached sleeve is passed from behind forward through axial bore 64, so that the front surface 34 of holder body 32 contacts an inner surface 65 of nose 66, preventing further forward movement of the holder body and attached sleeve with respect to the cartridge.

The cartridge can additionally include a takeup spool 79, for storage of the free ends of suture 20. When the apparatus is loaded, suture 20 is arranged to pass from the knot in front end 22 of pin 12, through pin axial bore 18, through out through hole 81 in the wall of plunger axial bore 47, and over and around spool 79. As the emplacement apparatus is withdrawn, leaving the fastener, with the suture attached, fixed in place in the bone hole, as described above with reference to FIGS. 1.1-1.4, the free end of the suture 20 pays off from the takeup spool.

Cartridge 62 is then removably attached to hand held means for urging the plunger 40 frontward with respect to the cartridge. In the configuration shown by way of example in FIGS. 3.1 and 3.2, the hand held means 70 consists of two handle elements 72, 74, slidably engaged to provide a comfortable pistol grip 80 by which the rear handle element 74 can be moved in a front-and-rear direction with respect to the front handle element 72 by squeezing the pistol grip 80. The front end 73 of the front handle element 72 is adapted for removably mounting the rear end 68 of cartridge 62, for example in bayonet fashion, as shown in FIGS. 3.1 and 3.2. The front end 75 of the rear handle element 74 includes a push rod 76 whose front end 77 abuts the rear end 50 plunger 40 when the handle elements are assembled and the cartridge is mounted onto the front end 73 of handle front element 72, as shown in FIG. 3.2.

Alternatively, an axial bore 79 can be arranged to pass rearward through push rod 76 and handle rear portion 74, as shown for example in FIGS. 3.1, for conducting the suture rearward from the knot at the front end of the pin all the way to the outside, as for example at the rear.

With the apparatus so assembled, the surgeon grasps the apparatus by the pistol grip, and directs the expandable sleeve to the desired depth into the predrilled hole in the bone. Then, while holding the apparatus in place, the surgeon squeezes the grip 80 sliding the rear handle element 74 frontward with respect to the front handle element 72, as indicated by the arrow 100. The push rod 76 presses against the rear end 50 of plunger 40, urging the plunger frontward with respect to the holder body 30, and thereby pressing the pin 12 into the axial bore of the sleeve 14, causing the sleeve to expand within the bone hole, and then causing the cylindrical blade 48 to sever the connection between the sleeve and the holder body, leaving the fastener fixed in the bone as described above with reference to FIGS. 1.2-1.4.

The emplacement apparatus of FIGS. 10.1-10.4 or 11.1-11.4 operates generally as described above with reference to FIGS. 3.1 and 3.2, except that the holder body 232 or 332 is connected at the rear by a snap-on interlock with the hand held means for urging the plunger frontward with respect to the expandable sleeve, rather than retained by way of a nose portion 66 of the cartridge 60.

Figure 101:
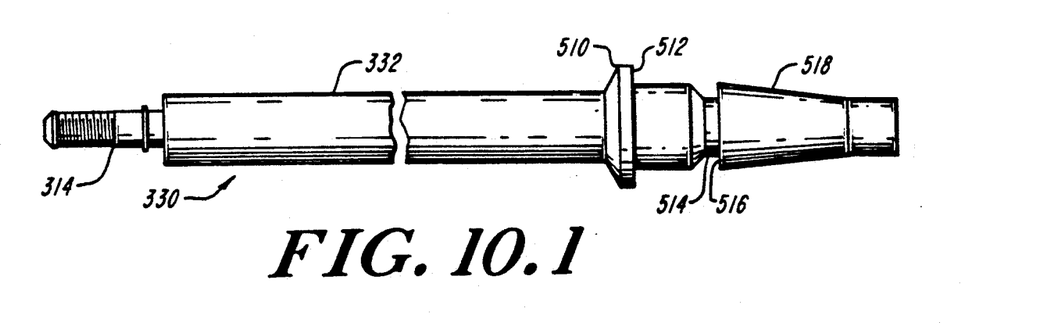
Figure 102:
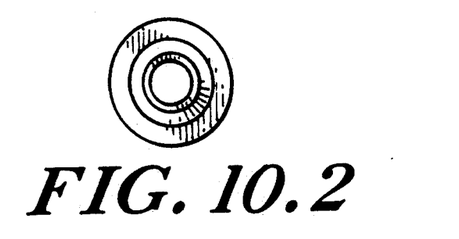
Figure 103:
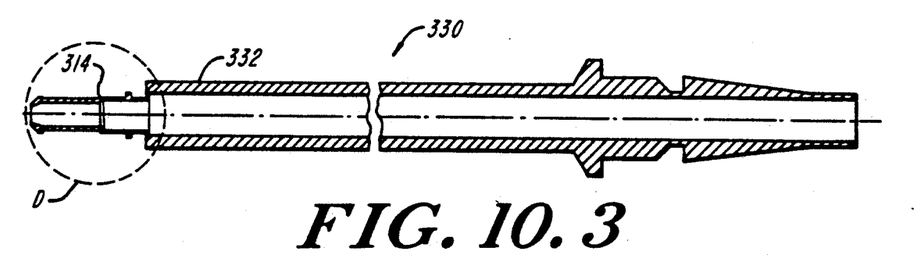
Figure 104:
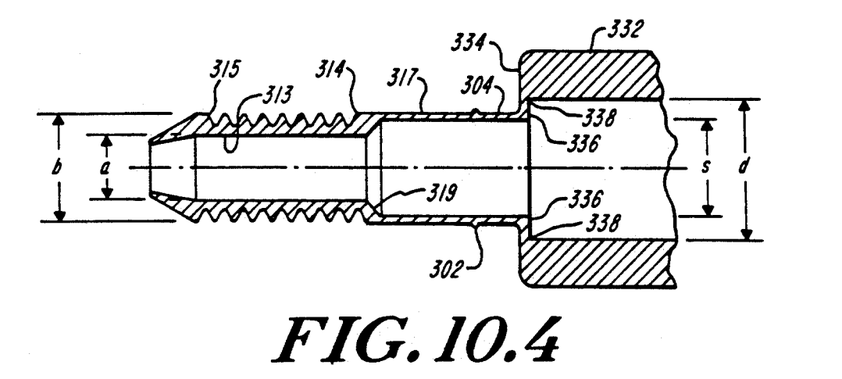
Figure 111:
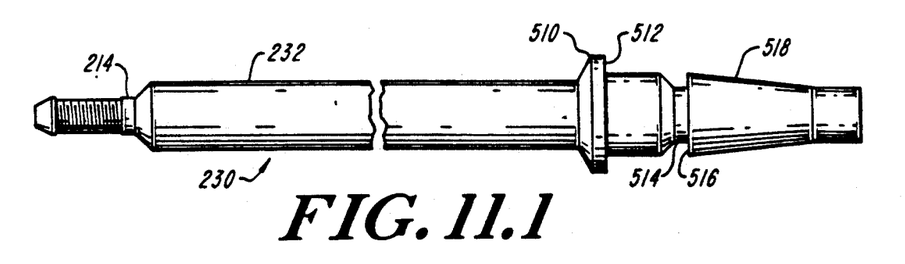
Figure 112:
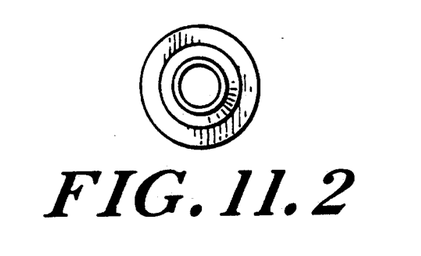
Figure 113:
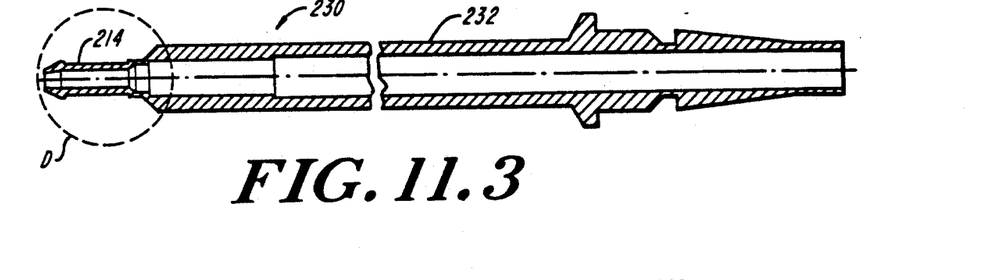
Figure 114:
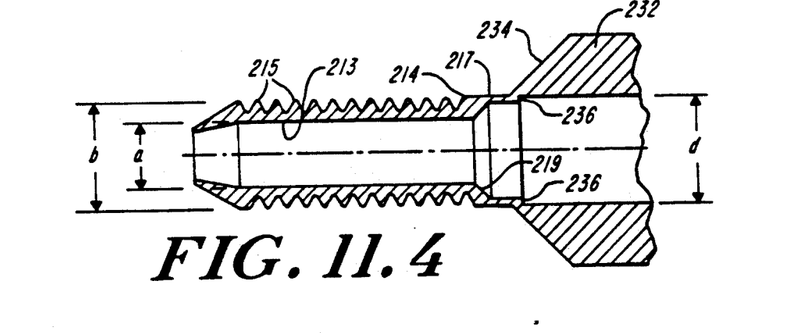
Figure 121:
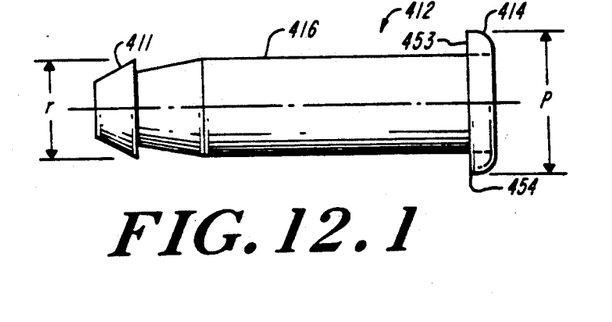
Figure 122:
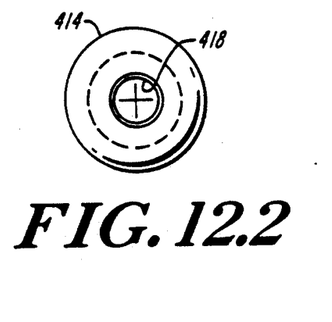
Figure 123:
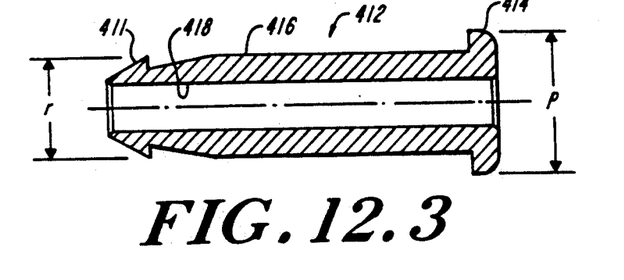

Preferably the snap-on interlock is configured as an insertible springloaded connector, in which a rear portion of the holder body forms the "male" part of the connector and a portion of the hand-held activator forms the "female" part. With reference now to either of FIGS. 10.1 or 11.1, a flange 510 is situated with a rear surface 512 situated a fixed distance rearward from the severable attachment of the expandable sleeve to the holder body. To the rear of the flange 510 is a groove 514 having a frontward-facing surface 516 generally perpendicular to the axis of the holder body, and the holder body tapers to rearward from the outer edge of the surface 516. The hand held means (not shown in the FIGS.) is provided with a generally cylindrical bore for receiving that portion of the holder body situated to the rear of the flange; and is provided with one or more keepers that are moved away from the axis by the advancing taper 518 and then spring into the groove 514 and lock against frontward-facing groove surface 516 when the rear portion of the holder body is correctly positioned within the receiving bore. The rear-facing surface 512 of the flange 510 contacts a part of the hand held means adjacent the holder body receiving bore, to provide a stop establishing the correct rearward position of the holder body within the hand held means. The hand held means is provided with a plunger that can be urged frontwardly with respect to the holder body receiving bore along the holder body axis, driving the pin before it toward and into the axial bore of the expandable sleeve.

Preferably the length of the plunger is fixed in relation to the fixed front-to-rear distance between the rear surface 512 and the severable attachment of the expandable sleeve to the holder body, and a stop is provided to limit the extent frontward to which the plunger can be urged within the hand held means, so that the separation of the expandable sleeve from the holder body is complete at just the point where the plunger has been moved to its frontmost limit. This ensures proper emplacement of the fastener in the bone hole, provided that the holder body is properly mounted in the handle and the user urges the plunger frontward as far as it will go.

EXAMPLE

Preliminary tests have demonstrated the effectiveness of prototype fastener and emplacement apparatus configured generally as described with reference to FIGS. 1.1-1.4, and made and dimensioned as follows (dimensional abbreviations are indicated on FIGS. 1.1 and 1.4).

The sleeve was formed of natural high density polyethylene ("PE"), type PDC 9122, supplied by Plastic Distributing Corp., and dimensioned to slide easily into a 3.5 mm (0.138 inch) diameter (c) bone hole. The outer surface of the sleeve was machined to a 6-32 screw thread configuration to provide protrusions, rather than annular ridges as shown in FIGS. 1.1-1.4, as screw threads are easier to form. A 6-32 screw thread configuration provides a 0.138 inch outermost diameter (b), so that the sleeve can be inserted into the 3.5 mm bone hole without resistance. The axial bore of the sleeve was of a uniform 0.090 inch diameter (a), and its length (f) was 0.138 inches.

The pin was formed of DuPont Delrin 100, machined to have the general shape shown in FIGS. 1.1-1.4, and an outermost diameter (g) of 0.125 inch. Delrin is much less deformable than the polyethylene of which the sleeve is made. The tapered leading edge of the pin permits the relatively incompressible pin to be forced into the 0.090 inch sleeve axial bore and to expand the relatively soft sleeve, generally as shown in FIG. 1.3. When the pin has been fully inserted within the sleeve, the device, as shown diagrammatically in FIG. 1.4, can have an outermost diameter (h) approximately 0.170 inch, providing for substantial deformation of the outer portions of the sleeve into the irregular wall of the bone hole, and thereby forming a firm fastener for the sleeve and pin. The pin has an axial bore of diameter 0.046 inches (i), which accepts a pair of sutures for later use in attaching soft tissue to the bone surface. Before insertion of the pin, the sutures are passed through the axial bore of the pin and their frontward ends are knotted so that they stop against the frontward end of the pin.

The outside configuration of the sleeve is a 6-32 thread which provides a series of ridges which assist in permitting deformation of the sleeve in the bone hole and conformation of the sleeve outer surface as it is pressed into the 0.138 inch diameter bone hole. In this prototype the threads are not used for turning the sleeve into the bone, but rather to facilitate deformation of the outer portion of the sleeve when the sleeve is expanded within the bone hole. When the hard delrin pin is pressed into the sleeve, the threads of the insert are deformed by irregularities in the hard cortical bone hole wall, locking the fastener, and the pin compressed within it, into place, as shown by way of example, and less diagrammatically than in the other FIGS., as described above with reference to FIG. 7.

The sleeve was formed with an annular connection to a cylindrical holder body as described above with reference to FIGS. 1.1-1.4, and enclosed within a cartridge and provided with emplacement apparatus as described above with reference to FIGS. 3.1 and 3.2, configured and dimensioned as follows.

The holder body was formed as a cylinder having inside diameter (d) 0.156 inch and outside diameter (j) 0.218, and length 0.420 inches. The connecting portion between the holder body and the rearward end of the sleeve was formed as an annulus having inside diameter 0.125 inches and outside diameter 0.218 inch, and lengthwise thickness (k) 0.012 inches.

The plunger and attachment severing means was constructed by positioning a stainless steel rod within a closely-fitting stainless steel tube, and machining the tube to provide a punch-and-die configuration generally as in FIGS. 1.2 and 1.3., having an outer diameter (l) 0.150 inch. The severing means was formed by machining the front end of the tube to form a sharpened step, located approximately 0.060 inches rearward from the blunt front end of the plunger; the tube wall had a thickness (m) about 0.012 inch.

As the plunger is pressed frontward, it presses the Delrin pin before it into the sleeve, expanding the sleeve and deforming it against the bone hole wall. When the pin approaches the point where it has been pressed fully into the sleeve, the sharpened step reaches the 0.012 inch thick connecting annulus and passes through it, shearing it and separating the fastener insert from the holding body. Then the emplacement apparatus is withdrawn together with the plunger and the holder body, leaving the fastener fixed within the predrilled bone hole.

A 3.5 mm (0.138 inch) diameter hole was made in the bone to a depth of 8 mm using a disposable spade drill with a stop to limit the hole depth. The prototype device was emplaced as described above with reference to FIGS. 3.1 and 3.2 in femur bone recovered from a pig cadaver, and then was tested as follows.

The hole was drilled into the pig femur cortical bone approximately normal to the bone surface to a depth about 8 mm using a step drill. Then a sutures was inserted into a cartridge and coupled to an installation tool, and positioned and fixed in the bone hole as described above. Then a knot was tied in the sutures at some distance from the fastener and looped over an Ametek Accuforce Cadet digital force gauge, 0–50 lbs. range (Mansfield & Green). The slack in the sutures was taken up by drawing the force gauge by hand away from the fastener in a direction perpendicular to the bone surface, and then the holding force was tested by sharply pulling the force gauge away from the bone by hand in a direction perpendicular to the bone surface. In such preliminary tests the fastener held, and the suture broke. These results demonstrate a holding capacity superior to those shown in similar tests using known devices now on the market. Apparently, the fastener according to the invention provides a superior platform to secure the fastener because it is locked into good dense bone, and because the conformity of the sleeve surface with irregularities in the bone provides a superior fixation. Moreover, there are no sharp edges in the fastener that can abrade the suture.

USE

The bone fastener according to the invention can be used for fastening to bone any of a variety of objects, including tissues such as ligaments or tendons and prostheses such as bone plates. The fastener and emplacement apparatus can be used in any of a wide variety of orthopedic surgical procedures and settings. The fastener can provide superior holding capacity and relatively small size, and can be installed according to the invention without hammering and without imposing any substantial net force toward or away from the bone surface, and so the invention provides for fastening in surgical settings in which bone anchors have not been used, or have been used with less success.

The fastener according to the invention is of a readily drillable material, and the installed fastener is situated near the bone surface. Thus, removal of the device from the bone in a later surgical procedure is straightforward. If removal of a fastener is indicated, the surgeon can simply use a drill, preferably of a somewhat smaller diameter than the original bone hole, to excavate the pin, and then the anchor and any debris can be simply withdrawn from the hole.

OTHER EMBODIMENTS

Other embodiments are within the following claims. For example the sleeve and pin can have other configurations and dimensions. The sleeve can, for example, be configured to fit in a bone hole having other than cylindrical shape. The fastener can be made smaller or larger than shown in the example, according to the size and characteristics of the bone at the particular fixation site. As a practical matter the lower limit of the fastener diameter depends upon providing a pin whose diameter is great enough that it can be forced without collapsing into the axial bore of the sleeve; for this reason a fastener can be made according to the invention having a smaller diameter, where the pin has no axial bore, as for example in headed rivet configuration. At the upper limit of size, as a practical matter a fastener requiring a very large hole in the bone may excessively compromise the bone structure itself, and in some circumstances a plurality of smaller fasteners according to the invention may be preferred over a single larger one. For rivet configurations, as for example in implantation of artificial ligaments, a fastener diameter as great as 10 mm or more may be desired.

Other fastener configurations are within the invention. For example, a fastener having the rear end of the sleeve configured to form a head can also be provided with a standoff, as shown for example in FIGS. 5 and 6. Referring now to FIG. 5, a fastener 90 with a head 92 and a standoff 94 between the head and the bone surface is shown fixed in bone and used to attach a ligament at the fixation site. The unexpanded sleeve can have its outer surface threaded over an extent that is to contact the bone hole wall, and left smooth over an extent between the threaded portion and the head. And, referring now to FIG. 6, the outer surface of the sleeve 100 can be configured to provide a stop 102 at the junction between the standoff 104 and the portion of the sleeve surface that contacts the bone wall, to limit precisely the depth to which the sleeve is inserted into the bone hole. Stop 102 can be formed, for example, as a pair of "ears", projecting far enough out from the sleeve so that they contact the bone surface at the edge of the bone hole, stopping the frontward progress of the sleeve further into the hole. When the surgeon senses the contact of the stop with the bone surface, the pin advancing mechanism can be activated, effecting fixation of the fastener at the predetermined depth. Standoff fasteners can be dimensioned to provide for various insertion depths and standoffs, according to the particular surgical setting.

Figure 41:
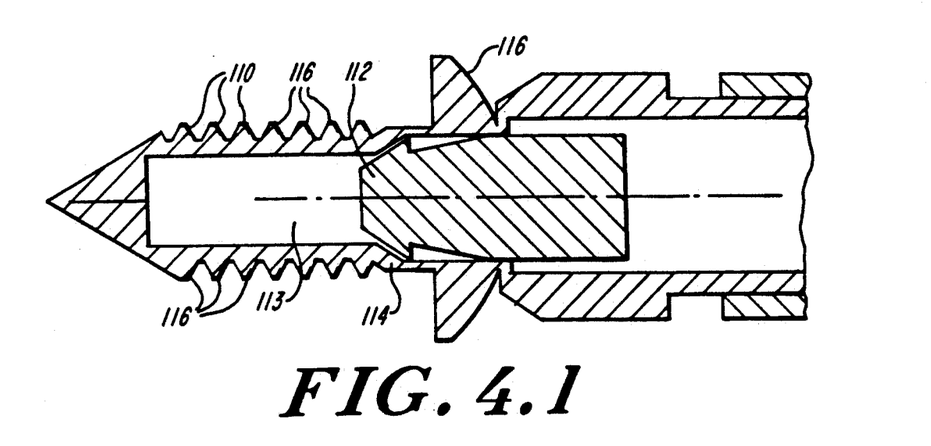

As shown in FIG. 4, the sleeve can be configured to be turned into the bone hole by self-tapping screw threads 110, and then fixed in place by forcing a pin 112 into the axial bore 113 of the sleeve 114 as described generally above. In this configuration, as in the others described herein according to the invention, fixation of the fastener in the bone hole is effected by the expansion of the sleeve in the hole, and the deformation of the sleeve and conformation of its outer surface with irregularities in the bone hole. The screw threads provide for positioning of the fastener in the hole at a desired depth, or for applying a desired force upon the object between the fastener head 116 and the bone surface, prior to fixation by forcing the pin into the axial bore in the sleeve.

In such a turnable screw thread configuration, the unexpanded sleeve can be turned into a bone hole having a diameter somewhat smaller than the outside diameter of the screw threads, so that the screw threads self tap the hole to some extent as the sleeve is turned into the hole, Although the threads are not meant to tap the bone hole to an extent sufficient by itself to effect firm fixation of the fastener, it can be useful to harden those surfaces of the screw threads that cut or abrade the bone hole wall, as for example thread edges and bearing surfaces 116. Such hardening can be provided, for example by forming the sleeve of a relatively deformable polymer material that can be hardened by application of heat or radiation, and then irradiating selective parts of the sleeve surface to harden it at those parts. Or, the softer sleeve can be provided over selected parts of its surface with a thin coating of a harder or more durable material. Once such a sleeve has been turned into the bone hole to the desired depth, the pin can be forced into the axial bore of the sleeve, expanding the sleeve, deforming the outer portion of the sleeve and redistributing the relatively harder surface portions so that the deformed surface substantially conforms to irregularities in the bone wall.

The sleeve can be made using any biocompatible material that results in a sleeve that expands in the bone hole when the pin is forced into the axial bore of the sleeve; and preferably the sleeve surface, when the sleeve is expanded outwardly, deforms and conforms to irregularities in the bone hole wall. The sleeve can be made using a combination of materials that provide the desired combination of properties for the particular configuration; for example, the head and standoff portion of a sleeve adapted for use as a rivet can be made of a less deformable material than the surface portion of the sleeve that conforms to the bone wall. And, as described above with reference to FIG. 6, the portions of the screw threads that in effect tap the bone hole as the sleeve is turned into the bone can be made of a harder material than the underlying sleeve mass.

Materials appropriate for manufacture of the sleeve include, for example, low density polyethylenes (PE 6010 and PE 2030) and polypropylene (13R9A and 23M2) (all Rexene, Dallas, Tex.) Of these, for example, PE 6010 and 13R9A have been FDA approved, as Class VI implant materials.

The pin can be made using any biocompatible material or combination of materials such that the pin is sufficiently incompressible that it serves to expand the sleeve outward against the cone hole wall when forced into the sleeve axial bore, and such that the pin can withstand the force of the plunger on its rear surface.

Besides biocompatible materials known at present, other materials whose biocompatibility has not yet been demonstrated can be used in the pin and the sleeve, and in the emplacement apparatus, as will be evident to those of ordinary skill. Ultem TM, for example, is a moldable, thermoformable polyetherimide polymer that has hardness, shear strength, and tensile strength characteristics that make it suitable for use in the pin; and moreover Ultem TM is autoclavable.

Configurations can be employed for the severable attachment between the holder body and the sleeve other than the complete annulus of severable material described above with reference to FIG. 1.3. For example, the attachment can consist of webbing between the holder body and the sleeve, or spokes 136 of severable material arranged at intervals between the holder body 32 and the sleeve 14, as shown for example in FIG. 8.1. Now the cutting tool, shearing tool, or heating means need sever only the spokes, as shown at 136' in FIG. 8.2. Or, a cutting tool, shearing tool, or heating element may be unnecessary where the severable attachment can be broken by applying force in a selective direction, as shown for example in FIGS. 9.1 and 9.2 In FIG. 9.1, holder body 32 is attached to sleeve 14 by a plurality of very attenuated spokes 236. The front-to-rear dimension of each of spokes 236 is sufficiently thick that it can withstand the counterforce required to balance the force of urging the pin into the sleeve axial bore. But the connection of the spoke to the sleeve 14 is thin enough so that, with the pin fully inserted into the sleeve, and the sleeve fixed in the bone hole, the holder body can be rotated about its long axis, as indicated by arrow 200 in FIG. 9.1, to break off the attachments as shown at 236' in FIG. 9.2, freeing the fastener from the holder body.

We claim:

1. Apparatus for emplacing a bone fastener in a bone, the apparatus comprising;
   an expandable sleeve having an axial bore defined therein, the expandable sleeve being configured to be insertible into a hole predrilled in the bone;
   a pin insertible into the axial bore, at least a portion of the pin having an outer diameter greater than an inner diameter of at least a portion of the axial bore;
   a holder for holding the expandable sleeve in position within the predrilled hole in the bone, the holder comprising a generally cylindrically shaped hollow body having a front and a rear end, said body being severably attached near its front end to the rear end of said expandable sleeve;
   a plunger moveable in relation to said holder for pressing the pin into said expandable sleeve axial bore without imposing substantial net forces toward or away from the bone; and
   means for severing said attachment between said holder and said expandable sleeve.

2. The apparatus according to claim 1, wherein the pin includes a head for retaining an object to be fixed to the bone.

3. The apparatus according to claims 1 or 2, wherein said means for severing includes a cylindrical blade having an annular cutting edge.

4. The apparatus according to claims 1 or 2, further comprising a hand-held means in communication with said holder for moving said plunger in relation to said holder.

5. The apparatus according to claim 4, wherein said holder includes an interlock portion at an end thereof for engagement with said hand-held means.

6. The apparatus according to claim 2, wherein said head of said pin comprises the means for severing.

7. The apparatus according to claim 1, wherein the holder body is severably attached to said expandable sleeve by an annular portion connecting said holder body front end to said expandable sleeve rear end.

8. The apparatus according to claim 7, wherein said annular portion comprises a plurality of severable material arranged at intervals between said holder body and said sleeve.

9. The apparatus according to claim 1, wherein said pin includes a suture.

* * * * *